United States Patent
Hedberg et al.

(10) Patent No.: US 7,085,602 B2
(45) Date of Patent: Aug. 1, 2006

(54) IMPLANTABLE BI-VENTRICULAR STIMULATION DEVICE AND SYSTEM, AND BI-VENTRICULAR STIMULATION AND SENSING METHOD

(75) Inventors: Sven-Erik Hedberg, Kungsängen (SE); Asa Uhrenius, Stockholm (SE); Karin Jarverud, Solna (SE); Hans Strandberg, Sundbyberg (SE); Nils Holmström, Järfälla (SE); Anders Björling, Järfälla (SE); Göran Budgifvars, Spanga (SE)

(73) Assignee: St. Jude Medical AB, Jarfalla (SE)

( * ) Notice: Subject to any disclaimer, the term of this patent is extended or adjusted under 35 U.S.C. 154(b) by 294 days.

(21) Appl. No.: 10/720,449

(22) Filed: Nov. 24, 2003

(65) Prior Publication Data

US 2004/0243187 A1 Dec. 2, 2004

(30) Foreign Application Priority Data

Dec. 16, 2002 (SE) .................................... 0203726

(51) Int. Cl.
*A61N 1/365* (2006.01)

(52) U.S. Cl. ........................................................ 607/9

(58) Field of Classification Search .................. 607/9, 607/11, 25, 66, 68; 600/509, 516–521
See application file for complete search history.

(56) References Cited

U.S. PATENT DOCUMENTS

| 5,720,768 | A | 2/1998 | Verboven-Nelissen |
| 6,070,100 | A | 5/2000 | Bakels et al. |
| 6,263,242 | B1 * | 7/2001 | Mika et al. ................. 607/9 |
| 6,370,430 | B1 | 4/2002 | Mika et al. |
| 6,424,866 | B1 * | 7/2002 | Mika et al. ................. 607/9 |
| 2002/0082650 | A1 | 6/2002 | Stahmann et al. |

FOREIGN PATENT DOCUMENTS

EP 1 123 716 8/2001

OTHER PUBLICATIONS

"Inhibition of Biventricular Pacing by Far-Field Left Atrial Activity Sensing: Case Report," Oguz, PACE, vol. 25, No. 10 (Oct. 2002) pp. 1517-1519.

* cited by examiner

Primary Examiner—George Manuel
(74) Attorney, Agent, or Firm—Schiff Hardin LLP

(57) ABSTRACT

An implantable bi-ventricular heart stimulating device (10) has a control circuit with first and second sensing circuits for respectively sensing in the two ventricles and first and second stimulation circuits for respectively stimulating the two ventricles. The control circuit determines whether a signal, sensed by said second sensing circuit, occurs essentially simultaneously with a signal sensed by the first sensing circuit. Furthermore, the control circuit determines whether a further signal is sensed by said second sensing circuit within a predetermined time interval which follows after the signal sensed by the second sensing circuit but within the same time cycle as that signal. If this occurs, the control circuit determines whether the sensed signals represent actual cardiac events, or are likely the result of far field detection.

19 Claims, 3 Drawing Sheets

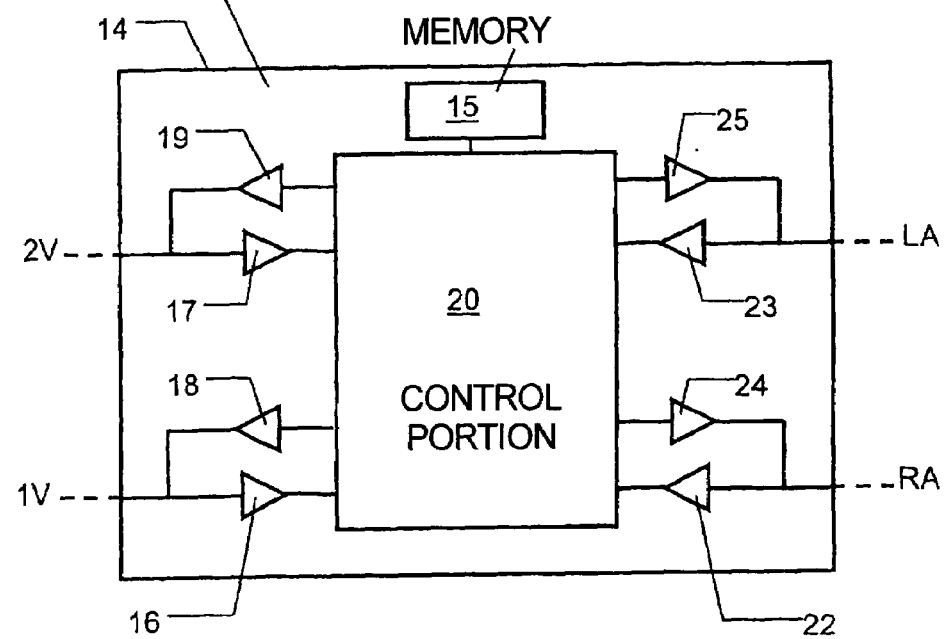
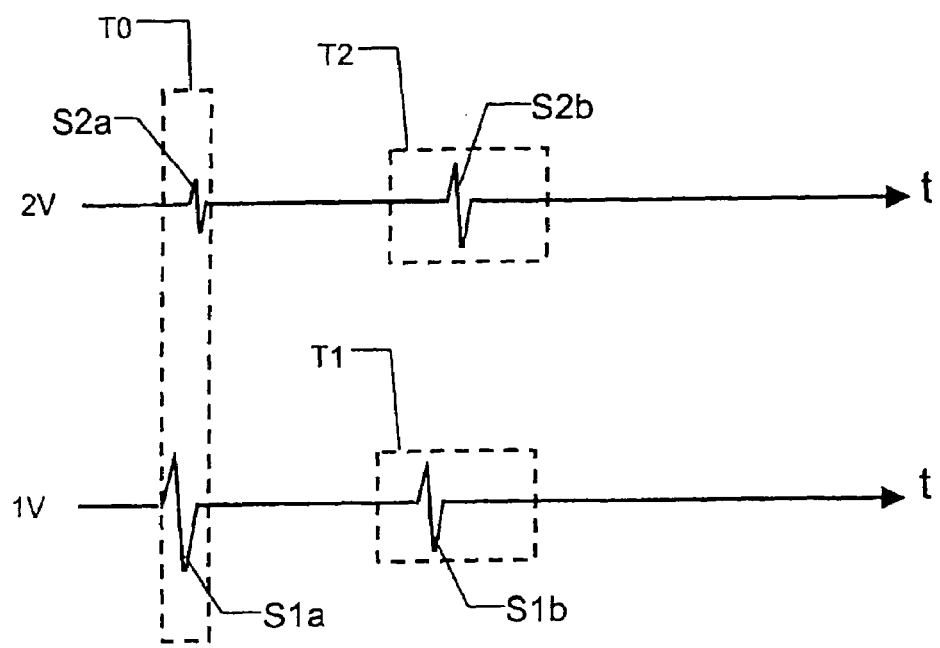

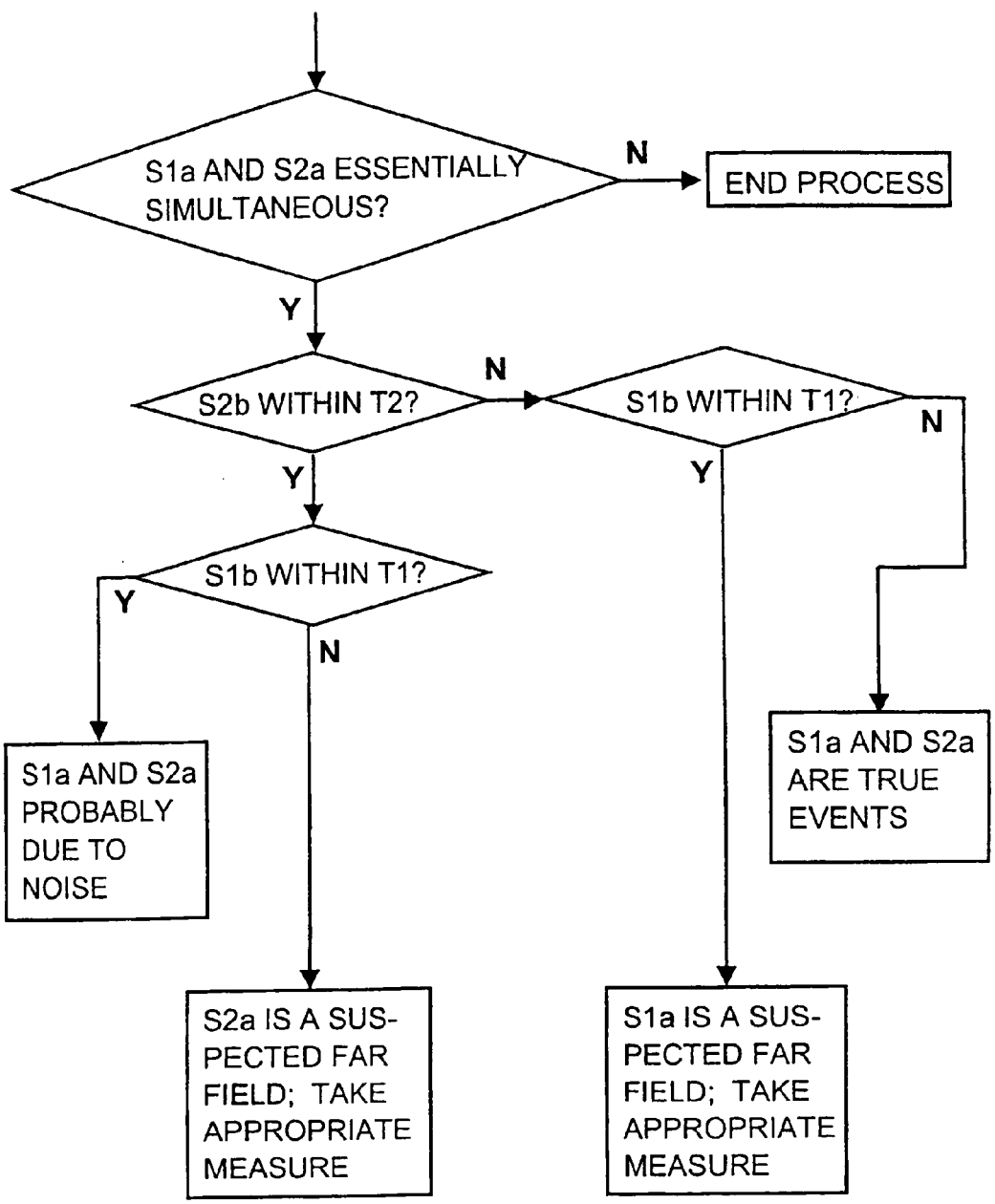

IMPLANTABLE BI-VENTRICULAR STIMULATION DEVICE AND SYSTEM, AND BI-VENTRICULAR STIMULATION AND SENSING METHOD

BACKGROUND OF THE INVENTION

1. Field of the Invention

The present invention relates to an implantable heart monitoring and stimulating device with which it is possible to stimulate both the ventricles of a heart, i.e. a bi-ventricular pacer. The invention also relates to a system including such a device and to a method for bi-ventricular stimulation and sensing.

2. Description of the Prior Art

Many different implantable devices for monitoring and stimulating a heart are known. Such devices are normally able to sense the electrical activity of the heart and to deliver stimulation pulses to the heart. Some implantable devices are able to sense, and deliver stimulation pulses to, both the left and right ventricles of the heart.

Devices that are able to deliver stimulation pulses to both the left and right ventricles are also called bi-ventricular pacers. Such devices can be used to treat patients who suffer from different severe cardiac problems, e.g. patients suffering from congestive heart failure (CHF). CHF is defined generally as the inability of the heart to deliver a sufficient amount of blood to the body. CHF can have different causes. It can be caused, for example, by a left bundle branch block (LBBB) or a right bundle branch block (RBBB). By using bi-ventricular pacing, the contraction of the ventricles can be controlled in order to improve the ability of the heart to pump blood. The stimulation pulses to the two ventricles can be delivered simultaneously but it is also known to deliver the stimulation pulses to the two ventricles with a short time delay between them in order to optimize the pumping performance of the heart.

U.S. Pat. No. 5,720,768 describes different possible electrode positions in order to stimulate or sense the different chambers of the heart.

U.S. Pat. No. 6,070,100 describes that electrodes may be positioned to sense and stimulate both the left atrium and the right atrium as well as the left and the right ventricles.

In connection with implantable heart stimulating devices, it is thus known to sense different signals using the implanted electrodes and to control the heart stimulating device in response to sensed signals. For example it is known to inhibit the delivery of a stimulating pulse if a natural, intrinsic, heart activity is detected. One difficulty in this context is to identify the signals that the device senses. Signals may originate from different intrinsic events in different parts of the heart. Signals also may originate from the heart stimulating device itself, i.e. from pulses delivered by different implanted electrodes. Signals may even have external causes, for example an external electromagnetic alternating field to which the person with the implanted device is exposed.

One kind of detected signal is a so-called far field signal. This is a signal that is detected by an implanted electrode, but which originates from some part of the heart other than that which is intended to be sensed with the electrode in question. This phenomenon is known in connection with pacers arranged to sense or stimulate both the right atrium and the right ventricle. For example, it is known that an electrode positioned in the right atrium may sense an R wave, i.e. a QRS complex, when this electrode actually should sense a P wave. The sensed R wave is thus in this case a far field signal. Different ways to avoid this problem have been suggested in connection with pacers arranged to sense or pace the right atrium and the right ventricle.

In connection with bi-ventricular pacers, or four chamber pacers, different kinds of problems concerning far field detection may occur than those known in connection with pacers arranged to sense or pace only the right atrium and the right ventricle.

SUMMARY OF THE INVENTION

The present invention is based on the recognition of a problem that may occur in an implantable heart stimulating device which has circuitry for sensing signals related to both the left ventricle and the right ventricle of a heart. The problem is that a signal detected in a ventricle could in fact originate from the other ventricle. In other words, the detected signal could be a far field signal from the other ventricle. An object of the present invention therefore is to provide an implantable heart stimulating device with which it is possible to distinguish a far field signal, which may originate from the other ventricle, from a signal from the ventricle which is intended to be sensed. The problem with a far field signal occurs when signals are detected essentially simultaneously by sensing circuitry designed to detect (sense) signals in the two ventricles.

The above object is achieved in accordance with the invention by an implantable heart stimulating device having a control circuit containing a memory, a first sensing circuit, adapted to be connected to a first sensing member suited to be positioned so as to transfer signals to said first sensing circuit for sensing cardiac events related to a first ventricle of the heart, and a second sensing circuit, adapted to be connected to a second sensing member suited to be positioned so as to transfer signals to the second sensing circuit for sensing cardiac events related to a second ventricle of the heart, the control circuit also includes a first stimulation circuit adapted to be connected to a first stimulation member for delivering stimulation signals to the first ventricle of the heart, and second stimulation circuit adapted to be connected to a second stimulation member for delivering stimulation signals to the second ventricle of the heart.

The control circuit also detects or determines a time cycle corresponding to a normal heart cycle. The control circuit executes the following procedure:

(a) determine whether, during a time cycle in which no stimulation signal is delivered by the second stimulation circuit, a signal S2$a$, sensed by the second sensing circuit, occurs essentially simultaneously with a signal S1$a$ sensed by the first sensing circuit, (b) determine whether a further signal S2$b$ is sensed by the second sensing circuit within a predetermined time interval T2 which follows after the signal S2$a$ but within the same time cycle as the signal S2$a$, wherein the predetermined time interval T2 starts 20–200 ms after the signal S2$a$, and (c) if both (a) and (b) occur, store in the memory an indication of the fact that the signal S2$a$, which constitutes a suspected far field signal, has been detected.

It should be noted that the aforementioned time cycle can be determined simply by defining a normal time for a heart cycle, for example about 1s, or by detecting events which signify a heart cycle. It should also be noted that the term "essentially simultaneously" means that the signals occur exactly simultaneously or that there is a very small time interval between them, for example less than 25 ms. If there is such a short time interval between the signals S1$a$ and S2a, then it is difficult to determine which sensing member is closest to the electrical activity. This means that there is a risk that, in this case, the signal S2a is a far field signal.

If the signal S2a is a far field signal, then there is a risk, according to this example, that the control circuit will interpret this signal S2a as if it is in fact an intrinsic signal originating from the second ventricle. Depending on the operation mode of the heart stimulating device, such a detected signal could influence the operation of the device. For example, such a signal could result in a stimulation pulse to the second ventricle being inhibited.

According to the invention, the aforementioned time interval T2 is monitored in order to detect whether a signal occurs within this time interval. A signal will occur in the time interval T2 if the signal S2a was in fact not an intrinsic signal from the second ventricle but a far field signal from the first ventricle, i.e. if no intrinsic depolarization has occurred in the second ventricle. However, the depolarization in the first ventricle will via the myocardium reach the second ventricle with a delay. It is such a delayed depolarization in the second ventricle that is sensed within the time interval T2. If the signal S2a was in fact an intrinsic depolarization in the second ventricle, then the second ventricle would be biologically refractory during the time interval T2 and no depolarization therefore could occur. A signal within the time interval T2 thus means that the signal S2a was in fact not an intrinsic depolarisation in the second ventricle but most likely a far field signal from the first ventricle.

In one preferred embodiment of the invention, the predetermined time interval T2 is 40–250 ms long, preferably 50–150 ms or 50–100 ms. The predetermined time interval T2 in one embodiment can start 50–150 ms after the signal S2a. The start and the length of the time interval T2 can be selected according to the particular case. Preferably, the time interval T2 occurs within the ventricular refractory period of implantable heart monitoring and stimulating device is often set to be about 230 ms. A suitable start and length of the time interval T2 thus depends on the expected time delay for the signal S2b to reach the second ventricle. In a particular case, this depends inter alia on the location of the electrode members when the device has been implanted in a living being.

The control circuit preferably is arranged to perform the procedure during a number of time cycles and to adjust the setting of at least one control variable of the device if the signal S2a, which constitutes a suspected far field signal, has been detected during at least a predetermined number of time cycles. The adjustment can be an increase of the sensing threshold. The predetermined number of time cycles could be, for example, 2, 5 or 10. The device alternative can operate such that the predetermined number of time cycles must occur within a certain time span in order for the device to adjust the setting of the control variable. For example, there could be a requirement that the predetermined number of time cycles occur within one minute or one hour. By increasing the sensing threshold, for example, the risk of far field sensing is reduced.

In another preferred embodiment, the control circuit also determines whether, during a time cycle in which no stimulation signal is delivered by the first stimulation circuit and no stimulation signal is delivered by the second stimulation circuit, in addition to the signal S2b also a signal S1b is detected, wherein the signal S1b fulfils the criteria of the signal S1b being sensed by the first sensing circuit within a predetermined time interval T1 which follows after the signal S1a but within the same time cycle as the signal S1a, this predetermined time interval T1 starting 20–200 ms after the signal S1a. The control circuit stores in the memory an indication that both the signal S1b and the signal S2b have been detected during a time cycle. In this embodiment, detection thus is done within both the time interval T1 and T2. If such signals are detected, this is an indication that the signals S1a and S2a are caused by an external interference. The device thus can take into account that an external interference probably exists.

It should be noted that the terms S1a, S2a, S1b, S2b, T1 and T2 are used herein only in order to distinguish the different signals and time intervals from each other.

Preferably, predetermined time interval T1 substantially coincides with the predetermined time interval T2.

The control circuit can set at least one timer period in response to detected signals S1a and/or S2a, and, when both the signal S1b and the signal S2b have been detected during a time cycle, the control circuit modifies the set timer period. The timer period that is set in response to detected signals S1a and/or S2a can involve the resetting of a timer period, and the modification can be that the resetting of the timer period is annulled.

In another aspect of the invention, an implantable heart stimulating system is provided having a device according to any of the above embodiments and first and second leads connected to the device. The first sensing member is arranged on the first lead and the second sensing member is arranged on the second lead. Preferably the first stimulation member is the same member as the first sensing member and the second stimulation member is the same member as the second sensing member. With such a system, the advantages described above are achieved.

The invention also concerns a stimulation and sensing method making use of such a system. According to this method, the system is implanted in a human or animal and the first sensing member is positioned in or at a first of the ventricles of the heart of the human or animal and the second sensing member is positioned in or at the second ventricle of the heart.

According to a preferred version of the method, the control circuit senses the signals S1a and S2a during a portion of the heart cycle where possible R-waves are expected to be sensed in the ventricles, and the above-described procedure is used to detect whether the signal S2a is in fact not a sensed R-wave from the second ventricle but a suspected far field signal from the first ventricle. Preferably, information about detection of one or more such suspected far field signals is stored in the memory such that this information is accessible to a physician at a medical check-up.

The system is used with advantage on a human or animal suffering from congestive heart failure, for example caused by a left or right bundle branch block. By using the system in the manners described above, appropriate measures may be taken in response to the detection of suspected far field signals.

BRIEF DESCRIPTION OF THE DRAWINGS

FIG. 2 schematically shows an inventive control circuit which may form part of the device of FIG. 1.

FIG. 3 schematically shows on a time scale signals sensed by first and second sensing circuits.

FIG. 4 is a simplified flow chart of the operation of the device.

DESCRIPTION OF PREFERRED EMBODIMENTS

Figure 1:
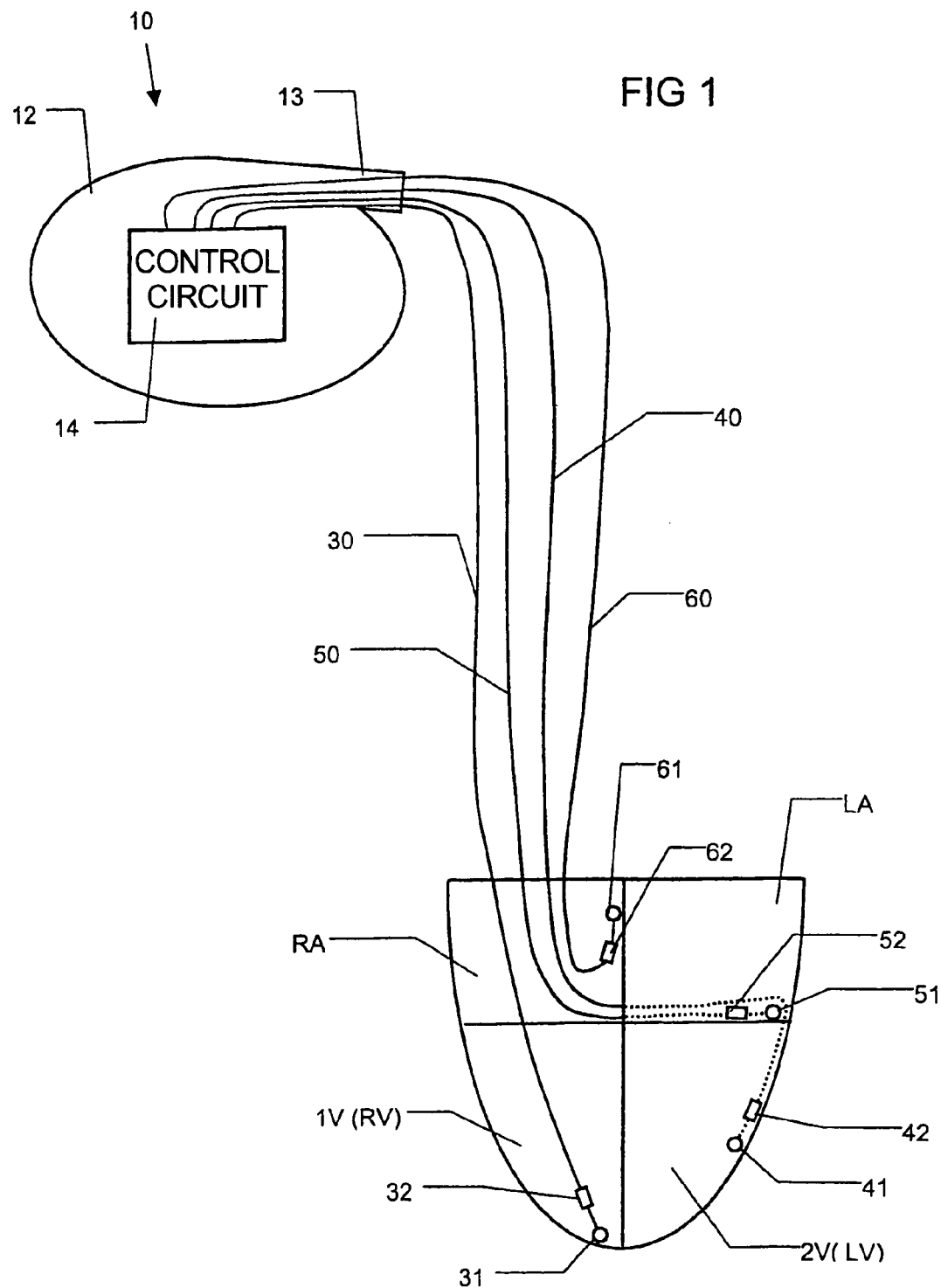
FIG. 1 schematically shows a heart stimulating system with a heart stimulating device connected to leads with sensing and stimulation members positioned in a heart.

FIG. 1 shows schematically an implantable heart stimulating device 10 according to the invention. The device 10 has a housing 12. The device 10 includes a control circuit 14 (that will be described more in connection with FIG. 2). The device 10 has a connector portion 13. The device 10 is in the illustrated embodiment connected to different leads 30, 40, 50, 60.

FIG. 1 also schematically shows a heart including a right atrium RA, a left atrium LA, a right ventricle RV and a left ventricle LV.

A first lead 30 includes electrode members 31, 32 positioned in the right ventricle RV of the heart. The electrode 31 may be a tip electrode and the electrode 32 can be a ring electrode. In this example, the first lead 30 thus includes bipolar electrodes. It is within the scope of the invention, however, for the device 10 to be connected to unipolar electrodes as is known to those skilled in the art. The electrodes 31, 32 constitute a first sensing member 31, 32 suited to sense cardiac events related to a first ventricle 1V (in this case the right ventricle RV). The electrodes 31, 32 also function as a first stimulation member 31, 32 for delivering stimulation signals to the first ventricle 1V.

A second lead 40 is connected to the housing 12. The second lead 40 includes in the shown embodiment bipolar electrodes 41, 42. These electrodes constitute a second sensing member 41, 42 positioned for sensing events related to the second ventricle 2V (in this case the left ventricle LV). The electrodes 41, 42 also constitute a second stimulation member 41, 42 for delivering stimulation signals to the second ventricle 2V. The second lead 40 may be introduced, for example, via the right atrium and the coronary sinus such that the member 41, 42 is positioned in, for example, the lateral posterior cardiac vein of the left heart. How to introduce the second lead 40 in this manner is known to those skilled in the art.

According to the shown embodiment, the device is also connected to a third lead 60 with electrode members 61, 62. These electrode members are positioned in the right atrium RA in order to be able to sense and stimulate this atrium. The device 10 in this case also is connected to a fourth lead 50 with electrode members 51, 52. These electrode members may be positioned in the coronary sinus in order to sense and stimulate the left atrium LA of the heart.

The housing 12 together with at least two leads 30, 40 thus constitute an implantable heart stimulating system 10.

FIG. 2 schematically shows the control circuit 14 in more detail. The control circuit 14 includes at least one memory 15. Furthermore, the control circuit 14 has a first sensing circuit 16 and a first stimulation circuit 18. These circuits are adapted to be connected to the first lead 30 in order to sense and stimulate the first ventricle 1V. The circuits 16, 18 also are connected to a control portion 20 of the control circuit 14.

The control circuit 14 also includes a second sensing circuit 17 and a second stimulation circuit 19. These circuits 17, 19 are adapted to be connected to the second lead 40 in order to sense and stimulate the second ventricle 2V. The circuits 17, 19 also are connected to the control portion 20 of the control circuit 14.

The control circuit 14 illustrated in FIG. 2 also has a third sensing circuit 22 and a third stimulation circuit 24. These circuits 22, 24 are adapted to be connected to the third lead 60 in order to sense and stimulate the right atrium RA. The control circuit 14 also includes a fourth sensing circuit 23 and a fourth stimulation circuit 25. These circuits 23, 25 are adapted to be connected to the fourth lead 50 in order to sense and stimulate the left atrium LA.

Since the components of a control circuit such as the control circuit 14 for controlling a pacer is well known to a person skilled in the art, no further details need to be described herein (other than the inventive operation thereof set forth below). FIG. 2 only functionally shows some of the components of the control circuit 14 and the control circuit 14 does not necessarily have to be designed in the manner indicated in FIG. 2. The control circuit 14 may of course include several other components. For example the control circuit 14 can control the heart stimulating device 10 by sensing the activity of the living subject into which the device 10 is implanted. Furthermore, the control circuit 14 can communicate via telemetry with an external device. The control circuit 14 also may include, for example, means for delivering defibrillation signals. The control circuit 14 may include several different memories, such as a RAM and a ROM. The memory 15 shown thus may be any suitable memory included in the control circuit 14. The memory 15 thus can be for example a RAM, where the signals are stored only for a very short time in order to control the operation of the device 10.

The control circuit 14 detects or determines a time cycle corresponding to a normal heart cycle. This can be done by detecting events in the heart corresponding to a heart cycle. It is also possible to determine a heart cycle by simply setting a time (for example about 1s) that corresponds to a normal heart cycle. The time can be set, for example, in response to a paced or sensed event and can thereby constitute an escape interval.

FIG. 3 schematically shows signals that may be detected by the first 16 and second 17 sensing circuits during a time cycle. The lower line in FIG. 3 refers to signals sensed by the first sensing circuit 16, i.e. primarily intended for sensing signals in the first ventricle 1V. The upper line in FIG. 3 shows signals detected by the second sensing circuit 17 during a time cycle, i.e. signals that are intended to originate from the second ventricle 2V. It should be noted that the first ventricle 1V can be either the left ventricle LV or the right ventricle RV. The second ventricle 2V is of course the other ventricle.

The control circuit 14 detects R-waves (i.e. a QRS complex) in the different ventricles. The control circuit 14 can be operated to detect such R-waves in a certain window, but preferably the control circuit 14 continuously monitors the respective ventricles 1V, 2V for the detection of R-waves, except for during short blanking periods. Normally, the control circuit 14 is also operated with a ventricular refractory period after the sensing of an R-wave (or after the delivery of a stimulation pulse). The purpose of detecting the R-waves is primarily in order to be able to control the operation of the device 10. For example, the detection of an R-wave may mean that a stimulation pulse is inhibited, i.e. that no stimulation pulse is delivered since an R-wave has been detected.

It should be noted that it is also possible to detect whether a delivered stimulating pulse actually results in a depolarization of the ventricle in question. Such detection is called capture detection. The present invention, however, is not concerned with such capture detection. Instead, the invention relates to the problem of determining whether a detected signal in a ventricle that is not stimulated, at least not during the time cycle in question, is actually a detected R-wave from this ventricle, and not, for example, a far field signal from the other ventricle.

FIG. 3 shows that the second sensing circuit 17 detects a signal S2a essentially simultaneously with a signal S1a detected by the first sensing circuit 16. In the example discussed it is assumed that no stimulation signal is delivered by the second stimulation circuit 19, at least not during the time cycle in question when S2a is detected. According to the invention, the control circuit 14 is arranged to determine whether a second signal S2b is detected by the second sensing circuit 17 during a predetermined time interval T2. The time interval T2 follows after the signal S2a but within the same time cycle as the signal S2a. The time interval T2 starts 20–200 ms after the signal S2a. The time interval T2 is preferably 40–250 ms long. If the signal S2a in fact represents a real R-wave in the second ventricle 2V, then no signal S2b would occur during the time interval T2, since the second ventricle 2V would be refractory during this time if S2a were a real R-wave. However, if the signal S2a does not represent a real R-wave in the second ventricle 2V, but S1a represents a real R-wave in the first ventricle 1V, then the R-wave in the first ventricle 1V will with a time delay reach the second ventricle 2V and will thereby be detected as the signal S2b. In other words, the signal S2b is an indication of the fact that the signal S2a is in fact not a signal that indicates an R-wave in the second ventricle 2V. Therefore it can be assumed that the signal S2a was a far field detection of the signal S1a. An indication of the fact that the signal S2a, which constitutes a suspected far field signal, has been detected is stored in the memory 15.

It should be noted that the time delay from the occurrence of the signal S1a to its detection as S2b in the second ventricle 2V depends on the particular case. This depends inter alia on the position of the electrode members 31, 32; 41, 42 in the heart. The delay can in some cases be as short as 20 ms but in other cases the delay can be, for example, 150 ms. Consequently, the start of the time interval T2 may depend on the particular case. One preferred starting point of the interval T2 is 50–150 ms, for example 60 ms, after the occurrence of the signal S2a. Also a suitable length of the time interval T2 may depend on the particular case. The time interval T2, for example, may be 50–150 ms long or 50–100 ms, for example 80 ms long.

The control circuit 14 preferably sets the time limit for when the detection S1a and S2a are considered as being essentially simultaneous. For example these signals can be considered to be simultaneous if the time interval between them is less than 25 ms. This requirement is in FIG. 3 indicated by the time window T0. T0 thus starts when S1a is detected, and has a length of, for example, 25 ms.

The control circuit 14 performs the above described procedure during a number of time cycles. The control circuit 14 can adjust the setting of at least one control variable of the device 10 if the signal S2a, which constitutes a suspected far field signal, is detected during at least a predetermined number of time cycles. The predetermined number of time cycles can be, for example, 1, 5 or 10 or any other suitable number. By detecting this type of signal S2a several times, it is more likely that the signal is in fact a far field signal. The control variable that is adjusted may be, for example, the sensing threshold of the second sensing circuit 17. This sensing threshold, for example, may be increased if a number of such far field signals S2a have been detected. By increasing the sensing threshold, the likelihood of detecting a far field signal is reduced. The sensing threshold of course should not be increased so much that the real R-wave in the second ventricle 2V is not detected. Normally the far field signal is much weaker than the real R-wave, however, if in a certain case the far field signal is as strong as the real R-wave from the second ventricle 2V, then the device can be automatically set to operate only in response to signals sensed in the first ventricle 1V.

In a further embodiment of the invention, the control circuit 14 also monitors whether a signal S1b is detected by the first sensing circuit 16. The control circuit 14 senses the second signal S1b during a time interval T1 that follows after the signal S1a and within the same time cycle as the signal S1a. The time interval T1 starts 20–200 ms after the signal S1a. Exactly when to start the time interval T1 may depend on the particular case. The time interval T1 may thus be set to start for example 50–150 ms after the signal S1a. The length of the time interval T1 may be for example 40–250 ms, preferably 50–150 ms or most preferred 50–100 ms. The control circuit 14 may operate with the predetermined time interval T1 substantially coinciding with the predetermined time interval T2. The sensing during the time interval T1 and also during the time interval T2 preferably is done during a time cycle when no stimulation signal is delivered by the first stimulation circuit 18 and no stimulation signal is delivered by the second stimulation circuit 19.

As explained above, the detection of the signal S2b normally means that the signal S2a was not a real R-wave. Analogously, the detection of the signal S1b ought normally to mean that the signal S1a was not a real R-wave. However, if neither S1a nor S2a is an indication of an R-wave this means that neither the first ventricle 1V nor the second ventricle 2V actually depolarized. If neither ventricle depolarized, then there can not be any transferred signals S2b and S1b. The occurrence of both the signals S1b and S2b therefore is an indication of the fact that the signals S1a and S2a probably have some other cause. For example, these signals may be caused by an external interference.

The control circuit 14 is normally arranged to set different time intervals, or to inhibit or deliver stimulation pulses, in response to detected signals S1a and S2a. However, the detection of both said signal S1b and the signal S2b during a time cycle is, as explained above, an indication of an external interference. Therefore, the control circuit 14 according to the present invention preferably operates to modify a set timer period if the signals S1b and S2b are detected during a time cycle. For example, the signals S1a and/or S2a may involve the resetting of a timer period, for example a ventricular refractory period. The control circuit 14 therefore can operate to annul the set timer period if the signals S1b and S2b are detected during a time cycle. According to the invention, an indication of the fact that both the signal S1b and the signal S2b have been detected during a time cycle is stored in the memory 15. The memory 15 may in this case only constitute a RAM memory wherein this indication is stored for a short time in order to control the device in an appropriate manner, such as to annul the resetting of the aforementioned timer period. It is also possible to store an indication in the memory 15 such that this indication can be transferred to an external device, for example in connection with a medical check-up.

FIG. 4 shows a simplified flow chart of the operation of the device 10. The algorithm is performed by the control circuit 14. It is determined whether a signal S1a and a signal S2a occur essentially simultaneously. If this is not the case, then the algorithm for detecting a suspected far field signal ends.

If, however, the signals S1a and S2a occur essentially simultaneously, then it is determined whether a signal S2b occurs within the time interval T2. If this is the case, then it is determined whether a signal S1b occurs within T1. If both a signal S2b and a signal S1b have been detected, then this is an indication of the fact that S1a and S2a are probably caused by noise, such as an external interference. The control circuit 14 then can take appropriate measures as described above. If, however, a signal S2b is detected but no signal S1b, then S2a is probably a far field signal and an appropriate measure according to the above description can be carried out.

If no S2b is detected within T2, then it is determined whether a signal S1b is detected within T1. If this is the case, then the signal S1a is probably a far field signal and an appropriate measure is carried out as described above. If the signals S1a and S2a occur essentially simultaneously, but neither S2b occurs within T2 nor S1b occurs within T1, then S1a and S2a are probably true events (true R-waves), and the operation of the device continues as normal.

It should be noted that, although not shown in FIG. 4, the control circuit 14 can operate such that the different measures are carried out only if the different situations occur a predetermined number of times.

The control circuit 14 preferably also maintains the information concerning detected far field signals in the memory 15 such that this information is available to a physician at a medical check-up.

In the flow chart of FIG. 4 a "yes" is indicated by Y and a "no" by N. It should be noted that the flow chart is a simplified algorithm. The control circuit 14 as mentioned above, can operate to check whether S2b is within the time interval T2 only during heart cycles where no stimulation pulse has been delivered by the second stimulation circuit 19.

The invention also concerns a method for bi-ventricular stimulation and sensing using the above described system. According to this method, the system is implanted in a human or animal and the first sensing member 31, 32 is positioned in or at a first ventricle 1V of the heart. The second sensing member 41, 42 is positioned in or at the second ventricle 2V of the heart. The system is used, as explained above, in order to detect whether a signal S2a is in fact not a sensed R-wave but a suspected far field signal from the other ventricle.

The system preferably is used on a human or animal suffering from congestive heart failure, for example caused by a left or right bundle branch block.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable heart stimulating device comprising:
 a control circuit having a memory;
 a first sensing circuit adapted for connection to a first sensing member, adapted to be positioned to interact with a first ventricle of a heart, to supply signals to said first sensing circuit for sensing cardiac events related to said first ventricle;
 a second sensing circuit adapted for connection to a second sensing member, adapted to be positioned to interact with a second ventricle of the heart, to supply signals to said second sensing circuit for sensing cardiac events related to the second ventricle;
 a first stimulation circuit adapted for connection to a first stimulation member, adapted to be positioned to interact with the first ventricle, to deliver stimulation signals to the first ventricle from the first stimulation circuit;
 a second stimulation circuit adapted for connection to a second stimulation member, adapted to be positioned to interact with the second ventricle, for delivering stimulation signals from the second stimulation circuit to the second ventricle; and
 said control circuit being operable with a time cycle corresponding to a normal cardiac cycle, and said control circuit performing an algorithm wherein said control circuit:
  (a) determines whether, during a time cycle in which no stimulation signal is delivered by said second stimulation circuit, a signal S2a, sensed by said second sensing circuit, occurs substantially simultaneously with a signal S1a sensed by said first sensing circuit,
  (b) determines whether a further signal S2b is sensed by the second sensing circuit within a predetermined time interval following said signal S2a, and within a same time cycle as said signal S2a, said predetermined time interval starting at a time between 20 and 200 ms after said signal S2a, and
  (c) if both (a) and (b) occur, said control circuit storing in said memory an indication that said signal S2a has been detected, said signal S2a, constituting a candidate as a far field signal.

2. An implantable heart stimulating device as claimed in claim 1 wherein said control circuit sets said predetermined time interval to a duration in a range between 40 and 250 ms.

3. An implantable heart stimulating device as claimed in claim 2 wherein the control circuits sets said duration of said predetermined time interval to a duration in a range between 50 and 150 ms.

4. An implantable heart stimulating device as claimed in claim 1 wherein said control circuit starts said predetermined time interval at a time in a range between 50 and 150 ms after said signal S2a.

5. An implantable heart stimulating device as claimed in claim 1 wherein said control circuit performs said algorithm in a plurality of time cycles and adjusts a control variable associated with at least one of stimulating and sensing at least one of said first and second ventricles, if said signal S2a is detected during a predetermined number of said time cycles.

6. An implantable heart stimulating device as claimed in claim 5 wherein said control variable is a sensing threshold of said second sensing circuit, and wherein said control circuit adjusts said sensing threshold by increasing said sensing threshold.

7. An implantable heart stimulating device as claimed in claim 1 wherein said control circuit additionally determines whether, during a time cycling which no stimulation signal is delivered by said first stimulation circuit and no stimulation signal is delivered by said second stimulation circuit, a signal S1b is detected in addition to said signal S2b, said signal S1b fulfilling the criteria of being sensed by said first sensing circuit within a predetermined time interval following said signal S1a and within a same time cycle as said signal S1a, said predetermined time interval starting at a time in a range between 20 and 200 ms after said signal S1a, and wherein said control circuit stores in said memory and indication that both said signal S1b and said signal S2b have been detected during a time cycle.

8. An implantable heart stimulating device as claimed in claim 7 wherein said control circuit causes said predetermined time interval associated with detection of said signal S1b to substantially coincide with said predetermined time interval associated with sensing of said further signal S2b.

9. An implantable heart stimulating device as claimed in claim 7 wherein said control circuit sets at least one timer period in response to detection of at least one of signals S1a and S2a and wherein, when said control circuit detects both said signals S1b and S2b during a time cycle, said control circuit modifies said timer.

10. An implantable heart stimulating device as claimed in claim 9 wherein said control circuit sets said timer period in response to detection of at least one of said signals S1a and S2a by resetting a timer period, and modifies said timer period by annulling resetting of said timer period.

11. An implantable heart stimulating system comprising:
a control circuit having a memory;
a first sensing member adapted to be positioned to interact with a first ventricle of a heart;
a first sensing circuit connected to said first sensing member to supply signals to said first sensing circuit for sensing cardiac events related to said first ventricle;
a second sensing member adapted to be positioned to interact with a second ventricle of the heart;
to supply signals to said second sensing circuit for sensing cardiac events related to the second ventricle;
a first stimulation member adapted to be positioned to interact with the first ventricle;
a first stimulation circuit connected to said first stimulation member to deliver stimulation signals to the first ventricle from the first stimulation circuit;
a second stimulation member adapted to be positioned to interact with the second ventricle;
a second stimulation circuit connected to said second stimulation member for delivering stimulation signals from the second stimulation circuit to the second ventricle; and
said control circuit being operable with a time cycle corresponding to a normal cardiac cycle, and said control circuit performing an algorithm wherein said control circuit:
  (a) determines whether, during a time cycle in which no stimulation signal is delivered by said second stimulation circuit, a signal S2a, sensed by said second sensing circuit, occurs substantially simultaneously with a signal S1a sensed by said first sensing circuit,
  (b) determines whether a further signal S2b is sensed by the second sensing circuit within a predetermined time interval following said signal S2a, and within a same time cycle as said signal S2a, said predetermined time interval starting at a time between 20 and 200 ms after said signal S2a, and
  (c) if both (a) and (b) occur, said control circuit storing in said memory an indication that said signal S2a has been detected, said signal S2a, constituting a candidate as a far field signal.

12. An implantable heart stimulating system as claimed in claim 11 wherein said first stimulation member is carried by said first lead and wherein said second stimulation member is carried by said second lead.

13. An implantable heart stimulating system as claimed in claim 12 wherein said first stimulation member and said first sensing member are a same member, and wherein said second stimulation member and said second sensing member are a further same member.

14. A method for bi-ventricular stimulation and sensing comprising the steps of:
providing a control circuit with a memory;
connecting a first sensing circuit adapted to a first sensing member and positioning said first sensing member to interact with a first ventricle of a heart, to supply signals to said first sensing circuit for sensing cardiac events related to said first ventricle;
connecting a second sensing circuit to a second sensing member and positioning said second sensing member to interact with a second ventricle of the heart, to supply signals to said second sensing circuit for sensing cardiac events related to the second ventricle;
connecting a first stimulation circuit to a first stimulation member and positioning said first stimulation member to interact with the first ventricle, to deliver stimulation signals to the first ventricle from the first stimulation circuit;
connecting a second stimulation circuit to a second stimulation member and positioning said second stimulation member to interact with the second ventricle, for delivering stimulation signals from the second stimulation circuit to the second ventricle; and
operating said control circuit with a time cycle corresponding to a normal cardiac cycle, and performing an algorithm in said control circuit comprising:
  (a) determining whether, during a time cycle in which no stimulation signal is delivered by said second stimulation circuit, a signal S2a, sensed by said second sensing circuit, occurs substantially simultaneously with a signal S1a sensed by said first sensing circuit,
  (b) determining whether a further signal S2b is sensed by the second sensing circuit within a predetermined time interval following said signal S2a, and within a same time cycle as said signal S2a, said predetermined time interval starting at a time between 20 and 200 ms after said signal S2a, and
  (c) if both (a) and (b) occur, storing in said memory an indication that said signal S2a has been detected, said signal S2a, constituting a candidate as a far field signal.

15. A method as claimed in claim 14 comprising the steps of, in said control circuit, sensing said signals S1a and S2a during a portion of a heart cycle wherein R-waves are expected to occur in said first and second ventricles, and employing said algorithm to detect whether said signal S2a is not a sensed R-wave from said second ventricle but is a far field signal candidate from said first ventricle.

16. A method as claimed in claim 15 comprising making said indication of said detection of said signal as to a accessible from said memory during a medical check-up.

17. A method as claimed in claim 14 comprising selecting said stimulation pulses delivered by said first and second stimulation circuits to treat congested heart failure.

18. A method as claimed in claim 14 comprising selecting said stimulation signals delivered by said first and second stimulation circuits to treat left bundle branch block.

19. A method as claimed in claim 14 comprising selecting said stimulation signals delivered by said first and second stimulation circuits to treat right bundle branch block.

* * * * *